US009291632B2

(12) United States Patent
Xu et al.

(10) Patent No.: US 9,291,632 B2
(45) Date of Patent: Mar. 22, 2016

(54) AUTOMATED PLATELET FUNCTION ANALYZER AND ITS ANALYTICAL METHODS

(71) Applicant: Sinnowa Medical Science & Technology Co., Ltd., Nanjing, Jiangsu (CN)

(72) Inventors: Xin Xu, Nanjing (CN); Ziquan Dong, Nanjing (CN); Ning Cao, Nanjing (CN); Xiang Li, Nanjing (CN); Fan Yu, Nanjing (CN); Weijie Yang, Nanjing (CN)

(73) Assignee: Sinnowa Medical Science & Technology Co., Ltd., Nanjing, Jiangsu (CN)

( * ) Notice: Subject to any disclaimer, the term of this patent is extended or adjusted under 35 U.S.C. 154(b) by 41 days.

(21) Appl. No.: 14/154,666

(22) Filed: Jan. 14, 2014

(65) Prior Publication Data

US 2014/0134051 A1  May 15, 2014

Related U.S. Application Data

(62) Division of application No. 13/641,484, filed as application No. PCT/CN2011/077120 on Jul. 13, 2011, now abandoned.

(51) Int. Cl.
| | |
|---|---|
| *G01N 33/86* | (2006.01) |
| *A61B 5/15* | (2006.01) |
| *A61B 5/157* | (2006.01) |
| *A61B 5/153* | (2006.01) |
| *A61B 5/155* | (2006.01) |
| *G01N 33/49* | (2006.01) |
| *G01N 33/00* | (2006.01) |
| *G01N 35/10* | (2006.01) |
| *G01N 35/00* | (2006.01) |

(52) U.S. Cl.
CPC ............. *G01N 33/86* (2013.01); *A61B 5/1405* (2013.01); *A61B 5/1427* (2013.01); *A61B 5/15003* (2013.01); *A61B 5/153* (2013.01); *A61B 5/155* (2013.01); *A61B 5/157* (2013.01); *A61B 5/150221* (2013.01); *A61B 5/150755* (2013.01); *A61B 5/150992* (2013.01); *G01N 33/49* (2013.01); *G01N 35/1004* (2013.01); *G01N 2035/00534* (2013.01); *G01N 2035/00544* (2013.01)

(58) Field of Classification Search
CPC ................ G01N 35/1004; G01N 2035/00534; G01N 2035/00544; A61B 5/1405; A61B 5/15003; A61B 5/150221; A61B 5/1427; A61B 5/153; A61B 5/155; A61B 5/150992; A61B 5/157
USPC ................ 422/73; 435/13; 530/413; 436/180
See application file for complete search history.

(56) References Cited

U.S. PATENT DOCUMENTS

| | | | |
|---|---|---|---|
| 5,716,796 A | 2/1998 | Bull et al. | |
| 6,043,871 A * | 3/2000 | Solen et al. | 356/39 |
| 6,123,119 A * | 9/2000 | Okumura | 141/34 |
| 2006/0166373 A1* | 7/2006 | Enoki et al. | 436/180 |
| 2006/0246528 A1* | 11/2006 | Swaim et al. | 435/13 |

FOREIGN PATENT DOCUMENTS

| | | |
|---|---|---|
| CN | 2695975 | 4/2005 |
| CN | 202126438 | 1/2012 |
| WO | 2006/116699 | 11/2006 |

* cited by examiner

*Primary Examiner* — Rebecca M Fritchman
(74) *Attorney, Agent, or Firm* — Rankin, Hill & Clark LLP

(57) ABSTRACT

An automated platelet function analyzer includes a sampling vessel, a preparation vessel, an analysis vessel, a sampling needle, a blood sample syringe, a platelet agonist syringe, an analysis solution syringe and a blood mixing device. A method for platelet analysis is also disclosed.

4 Claims, 2 Drawing Sheets

AUTOMATED PLATELET FUNCTION ANALYZER AND ITS ANALYTICAL METHODS

FIELD OF THE INVENTION

The present invention relates to medical equipment and its analytical methods, more particular to an automated platelet function analyzer and its analytical methods, which can be used to rapidly and consecutively detect the changes of blood platelet aggregation.

BACKGROUND OF INVENTION

Platelet, a type of particle blood constituent, is an important factor for the blood hemostasis and thrombosis. Conveniently and efficiently determining the numbers, volume, aggregation rate and other parameters of platelet, plays a significant role in the diagnosis, prophylaxis and treatment guidance of thrombosis and related diseases. With the development of technology and in-depth study on platelet, some of the single platelet category or functional testing instrument has been developed in various countries. Such as: existing platelet aggregation analyzer (just a single function to measure the platelet aggregation parameters. The existing analytical instruments mainly based on the principle of turbidimetric method or direct method by measuring the electrode resistance), hematology analyzers or blood cell analyzer (such equipment can only determine the platelet numbers, volume and so on, and not have the ability to measure the same blood platelet repeatedly, consecutively and automatically. That is to say they are unable to determine the platelet aggregation automatically). Therefore, so far an analytical instrument to determine the platelet aggregation rate based on the principle of automatically and consecutively measuring the blood platelets changes in blood sample treated by platelet agonist do not exist. There is no instrument to measure the platelet numbers, volume automatically and further determine the platelet aggregation rate and other multiple parameters simultaneously.

Traditional detection principle used by the platelet aggregation instrument is optical turbidimetry method or electric resistance method. Platelet aggregation detector based on optical turbidimetry method is more common. However, this detector needs a larger amount of blood (2 ml whole blood usually). Before examination it still is pre-requisite to separate plasma, which is a complicated and time-consuming operation. Platelet aggregation analyzer based on resistance method achieves the platelet aggregation rate by measurement of platelet aggregation changes on the electrode, which also needs more than 2 ml whole blood. Furthermore, both methods described above are rarely for clinical use due to a poor reproducibility.

SUMMARY OF THE INVENTION

The object of this present invention is to solve the technical problems of the prior art by providing an automated platelet function analyzer and its analytical methods.

To solve the technical problems mentioned above, the present invention discloses an automated platelet function analyzer including a sampling vessel, a preparation vessel, an analysis vessel, a sampling needle, a blood sample syringe, a platelet agonist syringe, an analysis solution syringe and blood mixing devices.

The sampling vessel is used to store blood samples and as a platelet aggregation reaction container. Generally the volume of the sampling vessel is 1-5 ml and the sample volume added by the sampling needle or blood sample syringe is 100-1000 μl each time.

The preparation vessel is used for the first blood sample dilution. Generally the volume of the preparation vessel is 5-20 ml and the sample volume added by the sampling needle or the blood sample syringe is 10-50 μl each time. The volume of the first dilution is 50 to 300 times of the sample volume dispensed.

The analysis vessel is used for the second blood dilution and the platelet number detection. Generally the analysis vessel volume is 5-20 ml. The volume of the second dilution is 50 to 300 times of the sample volume dispensed.

After the second dilution, the final concentration of platelets is $1/90000$-$1/10000$ of the original blood samples.

The blood mixing devices are used for mixing the blood samples in the sampling vessel, the preparation vessel and the analysis vessel.

The said platelet agonist syringe is connected to the platelet agonist container to inject platelet agonist into the sampling vessel.

The analysis solution syringe is connected to the analysis solution container to inject the analysis solution to the preparation vessel or the analysis vessel.

The sampling needle, the blood sample syringe, the platelet agonist syringe and the analysis solution syringe are driven by motors.

The sampling needle is connected to the blood sample syringe and the analysis solution syringe through pipes and valves.

After the sampling needle is connected to blood sample syringe, add the blood sample in sequence to sampling vessel, absorbing the blood samples from sampling vessel and transferring it to preparation vessel, absorbing the diluted blood samples from preparation vessel and transferring it to the analysis vessel.

After the said the analysis solution syringe is connected to the said sampling needle, the sampling needle will be cleaned.

The mixing devices according to the present invention are air pumps, which are separately connected to the sampling vessel, preparation vessel and analysis vessel through pipes and valves.

The internal diameter of pipe, which connected to the sampling vessel, is 0.2 mm-2 mm, and its inlet air flow rate is 1-20 ml/min.

The preferred air pumps according to the present invention are rotary pumps or mixing syringes.

The present invention as described includes a cleaner which is used to clean the outer surface of sampling needle. The cleaner automatically cleans the residual blood of the sampling needle surface every time after analysis to prevent the residual blood of the sampling needle surface from affecting the data analysis.

Preferably the present invention includes a waste liquid pump, which is connected to the sampling vessel, the preparation vessel, the analysis vessel and the cleaner. Waste liquid pump cleans each vessel and empties the residual object when the corresponding analysis is completed The present invention also discloses a platelet analysis method which includes the following steps:

Step 1: connecting the sampling needle and blood sample syringe, absorbing the blood sample and transferring it to the sampling vessel and mixing.

Step 2: by sampling needle and blood sample syringe quantitatively absorbing the blood sample from the sampling vessel, and then transferring it to preparation vessel.

Step 3: transferring the analysis solution to the preparation vessel, quantitatively making the first dilution by the analysis solution syringe and mixing.

Step 4: connecting the sampling needle to blood sample syringe, quantitatively, absorbing the blood sample from the preparation vessel and transferring it to the analysis vessel.

Step 5: transferring analysis solution to the analysis vessel by the analysis solution syringe, quantitatively making a second dilution and mixing.

Step 6: counting the original platelet numbers of the blood sample in the analysis vessel Step 7: Dispensing the platelet agonist into the sampling vessel by the platelet agonist syringe and mixing; the volume ratio between the blood sample and the platelet agonist is 1:1-20:1. Generally the platelet agonist is the aqueous solution of adenosine diphosphate or arachidonic acid, or epinephrine.

Step 8: repeating step 2 to step 5 with a certain time interval and counting the platelet numbers of the blood sample at each time point after dispensing the platelet agonist. The common interval is 30-300 s.

Step 9: comparing the numbers of platelet after dispensing platelet agonist at each time point with that of original platelet to achieve the platelet aggregation rate.

In consideration of the analysis accuracy and analysis equipment volume, the present invention adopts twice dilution method using the preparation vessel and the analysis vessel to complete the dilution. Compared to the traditional method of once dilution, this dilution has better detection accuracy.

In the present invention, preferably the blowing-air method is adopted to mix the blood sample. Traditional platelet analysis equipment can only analyze the numbers of platelets statically, which is unable to analyze the platelet aggregation ability at a certain time consecutively. Because there will be inhomogeneous platelet after a certain period of time, through a large number of comparative study the applicant of the present invention found the analysis results by blowing-air method is the most accurate. Certainly, mechanically stirring method, using sampling needle or other straw suction method can also mix the blood samples to be analyzed.

In the present invention, the analysis solution should not affect the platelet aggregation in blood samples, react with any component of the blood, and contain any particles or impurities. Generally, deionized physiological saline or analysis solution available on the market for blood cell analyzer can be accepted. The Preferred the analysis solution is of osmotic pressure similar to blood osmotic pressure.

In the present invention, the platelets information obtained after the first detection is the original state information. Thereafter the differences of detection due to platelet aggregation in blood samples will reflect individual platelet number and volume changes in the blood samples after the platelet agonist is dispensed, and then the original platelet numbers, volume and platelet aggregation change after dispensing the platelet agonist will be obtained.

Beneficial effects: prominent advantage of the present invention lies in using of whole blood directly and finishing the detection of the platelet aggregation rate without the separation of plasma. Furthermore required blood is less (Less than 500 ul). Able to obtain test results of each time point in a certain time by the direct detection of platelet number changes before and after dispensing platelet agonist and consecutive detection, the result of detection at each time point of a period can be achieved. The instrument detection process is completely automated, so the detection is convenient, fast, and rarely susceptible to human factors.

BRIEF DESCRIPTION OF THE DRAWINGS

The present invention will now be further described by referring to the accompanying drawings that illustrate the preferred embodiments of the invention, from which its advantages described above and/or other advantages will be evident.

DETAILED DESCRIPTION OF THE EMBODIMENTS

Figure 1:
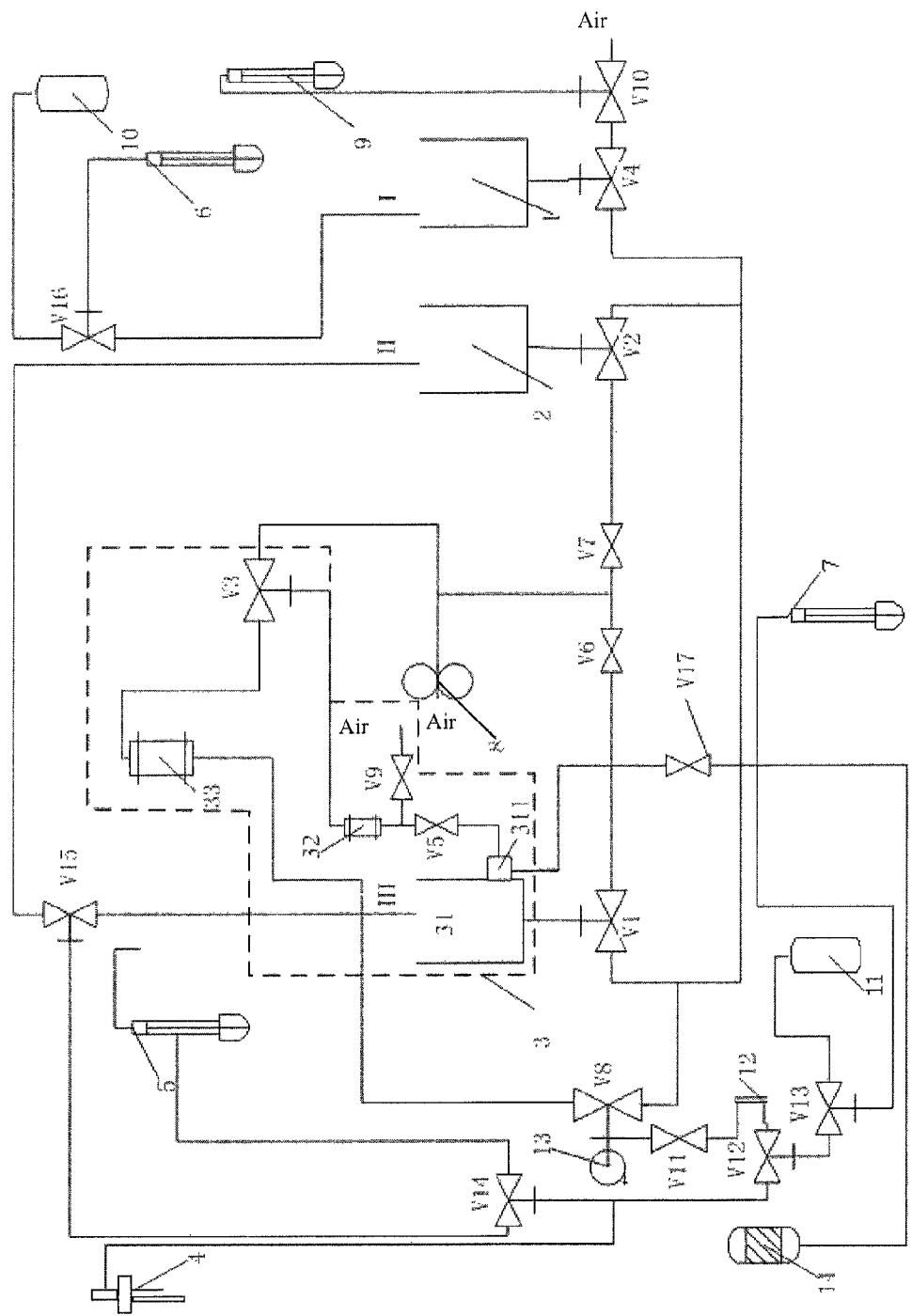
FIG. 1 is a schematic diagram of the instrument structure described in the present invention.

As shown in FIG. 1, the present invention disclose an automated platelet function analyzer comprising a sampling vessel 1, a preparation vessel 2, an analysis vessel 3, a sampling needle 4, a blood sample syringe 5, a platelet agonist syringe 6, an analysis solution syringe 7 and blood mixing devices. The sampling vessel is used to store blood samples. The preparation vessel is used for first dilution of the blood samples. The analysis vessel is used for the second dilution and the platelet number detection. The blood mixing devices are used to mix the blood samples in the sampling vessel, the preparation vessel and the analysis vessel. The platelet agonist syringe connected to the platelet agonist storage container 10 is used to inject platelet agonist into the sampling vessel. The analysis solution syringe connected to the analysis solution container 11 is used to inject analysis solution to the preparation vessel or analysis vessel. The sampling needle, the blood sample syringe, the platelet agonist syringe and the analysis solution syringe are driven by motors. The sampling needle is connected to the blood sample syringe and the analysis solution syringe through pipes and valves. After the sampling needle is connected with blood samples syringe, dispense the blood samples to the sampling vessel, absorbing the blood samples from the sampling vessel and transferring it to preparation vessel. Absorbing the diluted blood samples from preparation vessel, transferring it to the analysis vessel are carried out in sequence. After the analysis solution syringe is connected to the sampling needle, the sampling needle will be cleaned.

The mixing devices are air pumps, which are separately connected to the sampling vessel, the preparation vessel and the analysis vessel through pipes and valves.

The internal diameter of the pipe, which connected to the sampling vessel, is 0.2 mm-2 mm, and the inlet air flow rate is 1-20 ml/min.

The present invention includes a cleaner 12, which is used to clean the sampling needle outer surface.

The present invention includes a waste liquid pump, which is connected to the sampling vessel, the preparation vessel, the analysis vessel and the cleaner.

The present invention also discloses a platelet analysis method which includes the following steps:

Step 1: connecting the sampling needle with blood sample syringe, absorbing the blood sample, transferring it to the sampling vessel and mixing it.

Step 2: by using the blood sample syringe and the sampling needle quantitatively absorbing the blood sample from the sampling vessel, transferring it to the preparation vessel.

Step 3: analysis syringe dispenses analysis solution into preparation vessel to make the first dilution and mixture of the blood sample;

Step 4: connecting the sampling needle to the blood sample syringe, quantitatively absorbing the blood sample from the preparation vessel and transferring it to the analysis vessel.

Step 5: quantitatively making a second dilution by transferring the analysis solution to the analysis vessel through analysis solution syringe and mixing the blood sample.

Step 6: counting the original platelet numbers of the blood sample in the analysis vessel.

Step 7: dispensing platelet agonist into the sampling vessel by the platelet agonist syringe and mixing the blood sample;

Step 8: repeating step 2 to step 5 with a certain interval and counting the platelet numbers in the blood sample at each time point after adding platelet agonist.

Step 9: comparing the numbers of platelet after dispensing platelet agonist at each time point with that of original platelet to achieve the platelet aggregation rate.

Preferably the present invention adopts the blowing-air method to mixed blood sample.

EXAMPLE 1

As shown specifically in FIG. 1, the automated platelet function analyzer described in this example includes a sampling vessel 1. The sampling vessel is connected to the platelet agonist storage container 10 by platelet agonist pipe I and valve V16. At the same time valve V16 is connected with the platelet agonist syringe 6. The bottom of the sampling cup is connected to the mixing syringe through Valve V4 9 and the valve V8. Valve V10 is between valve V4 and the mixing syringe 9 and also connected to the outside air.

A preparation vessel 2 is connected with valve V15 by analysis solution pip II. Valve V15 is connected to valve 14, valve 12, valve 13 in sequence, finally to an analysis solution storage container 11. The bottom of the preparation vessel is connected to rotary pump 8 and valve V8 through valve V2. Valve V7 is between the rotary pump 8 and the valve V2.

Analysis vessel 3 is a combination of a set of equipment, Japanese sysmex production KX-21 Hematology analyzer can be used. Certainly you can also use specific structure in the following description. Both are of the same the principle. In terms of this embodiment, the said analysis vessel mainly includes vessel body 31, quantitative device 32 and vacuum vessel 33. Pipe III on the vessel body 31 for adding analysis solution is connected to valve V15. The bottom of vessel body 31 is connected to rotary pump 8 and valve V8 through valve V1. Valve V6 is between valve V1 and rotary pump 8. At the bottom of sidewall of the vessel body 31 is analysis hole 311. The analysis hole 311 is connected to a quantitative device 32 and a cleaning solution storage container 14 by pipes. The valve V15 and bypass valve V9 which connected to air are between an analysis hole 311 and a quantitative device 32. The quantitative device 32 is connected to the rotary pump 8 and the vacuum cup 33 by valve V3. The vacuum cup 33 is connected with valve V8 by pipes. Valve V17 is between the analysis hole 311 and the cleaning solution storage container 14. Cleaning solution in the cleaning solution storage container 14 is used to clean quantitative device 32 and vacuum cup 33.

The valve V8 is connected to waste liquid pump 13 and valve V11 simultaneously. The valve V11 is connected to cleaner 12. The cleaner 12 is connected to analysis solution storage container 11 by the valve V12 and the valve V13. The valve V13 is connected to analysis solution storage container 11 by pipes.

The sampling needle is connected to the valve 14 and the valve 12.

The blood samples syringe is connected to the valve 14.

In this embodiment without special description components are connected directly by pipes.

The process for the usage of this example:

Step 1: After sampling needle 4 is connected to the blood sample syringe 5 by the controlling valve V14 200-500 uL of whole blood as the blood sample is draw from the test tube equipped with a sodium citrate (Not shown in the figure). As the sampling needle moves into the sampling vessel 1 by controlling valve V14 the blood sample is injected into the sampling vessel. The mixing syringe 9 injects air to the bottom of sampling vessel 1 by controlling valve 10 and valve 4. The air mixes blood sample from the bottom to top. During this time the sampling needle 4 moves to the cleaner 12, and by controlling valve V12 and valve V13. The cleaner cleans the outer surface of the sampling needle with cleaning solution to remove residual blood of outer surface, and by controlling the blood sample syringe 5 cleans the inner surface of the sampling needle with analysis solution to remove residual blood of inner surface.

Step 2: After sampling needle 4 is connected to blood sample syringe 5 by the controlling the valve V14, 10-30 uL mixed blood sample is absorbed from the sampling vessel and transferred into the preparation vessel 2.

Step 3: Through analysis solution syringe, sampling needle and analysis solution pipe II 3.25 ml analysis solution is transferred to the preparation vessel for the first dilution by the controlling valve V13, the valve V12, the valve V14 and the valve V15. Analysis solution can be transferred by analysis solution syringe, sampling needle and analysis solution pipe III. This example adopts both means simultaneously. Rotary pump 8 inject air to the bottom of preparation vessel mix the first dilution sample by controlling valve V7 and valve V2. During this time the sampling needle 4 moves to the cleaner 12, the cleaner cleans the outer surface of the sampling needle with cleaning solution by controlling valve V12 and valve V13 to remove residual blood of outer surface and clean the inner surface of the sampling needle with analysis solution by controlling blood sample syringe 5 to remove residual blood of inner surface.

Step 4: After sampling needle 4 is connected to blood sample syringe 5 by the controlling valve V14, 10~30 uL of the first dilution blood sample is absorbed from the preparation vessel and transferred to the analysis vessel 3.

Step 5: By controlling valve V13, valve V12, valve V14 and valve V15, 3.25 ml analysis solution through analysis solution syringe, sampling needle and analysis solution pipe III is added into the analysis vessel for the second dilution. The analysis solution can be transferred by the analysis solution syringe, the sampling needle or the analysis solution pipe III. This example adopts both means simultaneously. The rotary pump 8 injects air to the bottom of preparation vessel to mix the second dilution sample by controlling valve V6 and valve V1. The waste liquid pump 13 vacuums the vacuum vessel 33 to form a negative pressure by valve 8 and vacuum vessel absorbs the blood sample of the secondary dilution in the analysis vessel from the analysis hole 311 by the valve V3 and the valve V5. The quantitative device 32 ensures that the same amount of liquid is absorbed out each time. After the detection is finished by controlling valve V9 open and close the negative pressure in pipe is released and pipeline inside has a same pressure with environment.

Step 6: The numbers of original platelet of the blood sample in the analysis vessel is determinated.

At the end of the tests by controlling valve V13, valve V12, valve V14, valve V15 analysis solution syringe 7 adds 4 ml analysis solution to the preparation vessel 2 and the analysis vessel 1 respectively, which is soaked for the next test. The waste liquid pump 13 empties the preparation vessel 2 by controlling valve the V8 and the valve V2 and empties the analysis vessel 3 by controlling the valve V8 and valve V1 before the next test.

Step 7: The platelet agonist syringe 6, platelet agonist storage container 10 and platelet agonist pipe I are connected by controlling valve V16, and 10-50 ul platelet agonist is added into sampling vessel 1. By controlling valve V4 and valve V10 Mixing syringe 9 is connected to and sampling vessel 1 and air is injected into the bottom of sampling vessel 1 to mix the blood sample after platelet agonist is dispensed. An internal diameter of the pipe is 1 mm and the inlet air flow rate is 1~20 ml/min.

Step 8: Step 2 to step 5 are repeated every 60 s. The blood sample added platelet agonist is drawn into the preparation vessel and analysis vessel in sequence and second quantitative dilution is done and the blood sample is mixed. The numbers of blood platelet in analysis vessel at each time point are determined after platelet agonist is dispensed.

Step 9: The numbers of platelet of the blood sample at each time point after dispensed platelet agonist are compared with the numbers of the original platelet to achieve the platelet aggregation rate.

After determination through valve V13, valve V12, valve V14 and valve V15, the analysis solution syringe adds 4 ml analysis solution into preparation vessel 2 and analysis vessel 1 respectively 7 which is soaked for the next test.

The analysis solution syringe 7 adds 2 ml analysis solution to sampling vessel 2 by valve V13, valve V12, valve V14 and sampling needle pipe. Then the waste liquid pump 13 empties the sampling vessel by controlling valve V8 and valve V4. The step is repeated for 3 times in order to clean the sampling vessel for the analysis of next blood sample.

In this embodiment analysis solution should been maintained at a constant temperature (a certain temperature between 18~39° C. Temperature changes of reagent should not larger than ±1.5° C.). A constant temperature can be achieved by previously heating reagent bottles, pipes at the early position of preparation vessel and analysis vessel with heating device, or combined previously heated reagent bottles and heated pipes and coupled constant temperature facilities with sampling needle, sampling vessel, preparation vessel and analysis vessel to make sure the temperature not lower than 18° C. during the analysis. Temperature changes of various aspects should not be larger than ±1.5° C. Means to achieve the goal can be by adding constant temperature facilities of all related components or designing constant temperature equipment inside the instrument

EXAMPLE 2

The repeatability of platelet aggregation rate measured by an automated platelet function analyzer and the comparison of platelet aggregation rate with turbidimetric method.

Comparison between the repeatability of results from an automated analyzer according to the present invention and that from a kind of instrument based on the principle of turbidimetric method (The turbidimetric method refers to: Born GVR. Aggregation of blood platelets by adenosine diphosphate and its reversal. Nature (Lond.). 1962; 194: 927) Using one whole blood sample with citrate sodium as anticoagulant, the platelet aggregation rates from 0 to 5 min are determined respectively by the analyzer according to the present invention and turbidimetric method instrument. The repeated 10 results showed in the table below.

The instrument mentioned in this embodiment is the same as that mentioned in example 1. Operation steps is also the same as that mentioned in embodiment 1. Analysis solution is physiological saline. Platelet agonist is diphosphate adenosine aqueous solution. The first dilution ratio is 240 times, and the second dilution ratio is 240 times.

TABLE 1

The platelet aggregation rate from 1 to 5 minutes determined from the instrument according to the present invention (instrument model: PL-11)

| items | Original platelet count ($\times 10^9$/L) | The platelet aggregation rate (%) | | | | |
|---|---|---|---|---|---|---|
| | | 1 min | 2 mins | 3 mins | 4 mins | 5 mins |
| test 1 | 145 | 35.0 | 43.0 | 54.6 | 62.3 | 61.4 |
| Test 2 | 142 | 34.6 | 40.6 | 52.8 | 65.8 | 67.3 |
| Test 3 | 140 | 36.3 | 45.5 | 56.2 | 60.1 | 65.5 |
| Test 4 | 146 | 33.6 | 41.9 | 55.4 | 64.5 | 63.8 |
| Test 5 | 142 | 38.9 | 47.0 | 57.6 | 65.4 | 64.7 |
| Test 6 | 148 | 37.1 | 42.5 | 55.9 | 60.1 | 62.3 |
| Test 7 | 141 | 34.3 | 44.6 | 55.4 | 62.5 | 60.8 |
| Test 8 | 150 | 35.6 | 41.0 | 53.2 | 64.0 | 62.4 |
| Test 9 | 144 | 33.2 | 46.2 | 57.6 | 59.9 | 63.9 |
| Test 10 | 151 | 34.8 | 44.1 | 55.1 | 62.4 | 64.8 |
| CV | — | 4.8% | 4.7% | 2.9% | 3.5% | 3.1% |

According to the 10 testing results the SD and average value at each minutes is worked out, then the Coefficient of variation (CV)

$$CV = SD/\text{average value} \times 100\%$$

In 1-5 min, all the repeatability of the 10 testing result of the platelet aggregation rate (Represented in CV) is not more than 5%, suggesting that the instrument possesses a reliable reproducibility in the use for determining platelet aggregation rate,

TABLE 2

The results of platelet aggregation rate (A platelet aggregation analyzer based on turbidimetric method)

| items | The platelet aggregation rate (%) | | | | |
|---|---|---|---|---|---|
| | 1 min | 2 mins | 3 mins | 4 mins | 5 mins |
| test1 | 24.5 | 29.0 | 36.6 | 50.3 | 50.4 |
| Test2 | 20.6 | 35.6 | 44.8 | 43.8 | 57.3 |
| Test3 | 20.3 | 40.5 | 38.2 | 48.1 | 49.5 |
| Test4 | 18.9 | 26.9 | 37.4 | 55.5 | 53.8 |
| Test5 | 26.5 | 32.0 | 49.6 | 46.8 | 46.7 |
| Test6 | 20.6 | 30.4 | 42.6 | 50.5 | 50.5 |
| Test7 | 27.1 | 35.1 | 34.3 | 45.6 | 55.9 |
| Test8 | 23.5 | 28.2 | 32.8 | 43.3 | 54.3 |
| Test9 | 22.6 | 27.8 | 37.8 | 36.9 | 57.1 |
| Test10 | 19.2 | 34.6 | 37.6 | 47.6 | 59.5 |
| CV | 13.1% | 13.6% | 12.9% | 10.7% | 7.6% |

The repeatability of the 10 test result of platelet aggregation rate in 1-5 min (represented in CV) is more than 10%, suggesting that instrument base on the urbidimetric method possesses a lower reproducibility than the instrument according to the present invention.

2) Correlation of results from the automated analyzer according to the present invention and turbidimetric method instrument 40 samples are determined by the automated analyzer according to the present invention and traditional turbidimetric instrument simultaneously. Maximum of platelet aggregation rate from the 40 samples is as follows:

TABLE 3

Comparison of the maximum platelet aggregation rate from automated analyzer according the present invention and turbidimetric instrument

| sample | Maximum platelet aggregation rate (%) | |
|---|---|---|
| | automated analyzer according the present invention | a traditional turbidimetric instrument |
| 1 | 75.5 | 61.7 |
| 2 | 56.1 | 50.2 |
| 3 | 54.3 | 48.1 |
| 4 | 66.8 | 59.3 |
| 5 | 45.2 | 36.5 |
| 6 | 69.1 | 61.5 |
| 7 | 77.2 | 63.7 |
| 8 | 48.1 | 40.8 |
| 9 | 28.5 | 23.1 |
| 10 | 78.7 | 62.9 |
| 11 | 65.2 | 58.2 |
| 12 | 51.2 | 40.8 |
| 13 | 49.4 | 34.8 |
| 14 | 62.3 | 49.2 |
| 15 | 51.5 | 44.3 |
| 16 | 65.6 | 53.9 |
| 17 | 54.2 | 43.9 |
| 18 | 46.8 | 42.6 |
| 19 | 78.4 | 62.2 |
| 20 | 68.9 | 54.6 |
| 21 | 43.6 | 33.5 |
| 22 | 65.9 | 59.1 |
| 23 | 69.6 | 55.8 |
| 24 | 39.2 | 30.3 |
| 25 | 45.8 | 40.4 |
| 26 | 57.6 | 45.9 |
| 27 | 49.2 | 39.1 |
| 28 | 46.5 | 39.1 |
| 29 | 54.8 | 49.2 |
| 30 | 34.6 | 25.9 |
| 31 | 63.8 | 57.8 |
| 32 | 68.6 | 59.1 |
| 33 | 54.2 | 47.5 |
| 34 | 53.0 | 39.8 |
| 35 | 62.8 | 44.6 |
| 36 | 51.2 | 37.8 |
| 37 | 65.9 | 48.9 |
| 38 | 59.3 | 53.7 |
| 39 | 58.2 | 52.8 |
| 40 | 46.8 | 42.6 |
| Average platelet aggregation rate | 57.1 ± 11.9 | 47.4 ± 10.5 |

Figure 2:
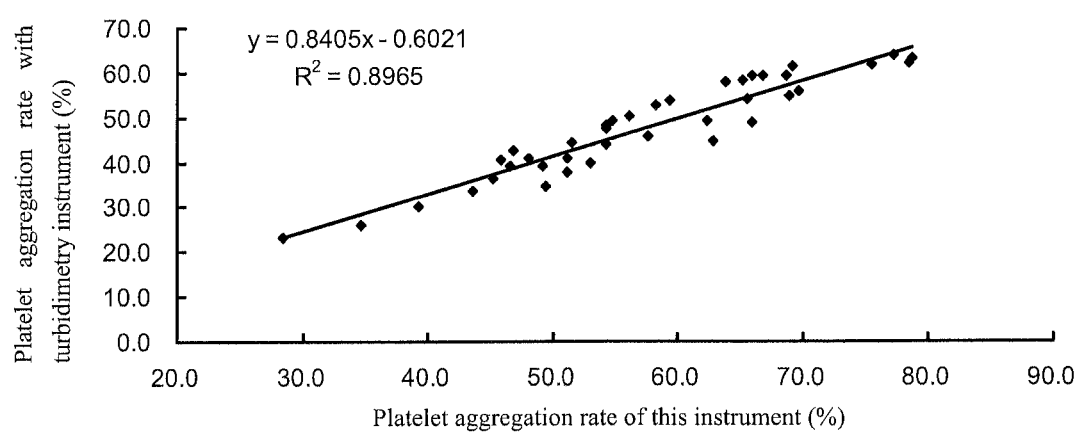
FIG. 2 is a correlation analysis of maximum platelet aggregation rate of the instrument described in the present invention and turbidimetry instrument.

The scatter chart was drawn with determination results of the automated analyzer as x-axis, and determination results of turbidimetric method instrument as y-axis. Meanwhile through linear regression analysis FIG. 2 is drawn. According to the results of FIG. 2, determination results from the two methods have a good correlation. Correlation coefficient is $R2=0.8965$, $R=0.9468$. But the determination results of the automated analyzer according to the present invention are higher than that of turbidimetric instrument. There is significant differences between them ($P<0.05$).

The automated platelet function analyzer according to the present invention can determine multiple parameters such as the numbers of platelet, mean platelet volume, platelet volume distribution, platelet aggregation rate (including platelet aggregation rate in different time, the maximum aggregation rate and the maximum aggregation time) and so on automatically and simultaneously. The test items are more efficient and more comprehensive. The automated analyzer can add platelet agonist automatically. Therefore, the instrument has the ability to obtain the platelet aggregation results at each time point by the direct detection of platelet changes before and after adding platelet agonist.

The present invention provides an idea for designing an automated platelet function analyzer and its analytical methods.

While preferred embodiments of the invention have been shown and described, there are many ways to realize this technical programme. It will be obvious to those skilled in the art that changes and modifications may be made without departing from the invention in its broader aspects, and therefore, the aim in the appended claims is to cover all such changes and modifications as fall within the true spirit and scope of the invention. Other parts not expressed in the embodiments can be achieved with existing technology.

The invention claimed is:

1. An automated platelet function analyzer comprising:
    a sampling vessel, a preparation vessel, an analysis vessel, a sampling needle, a blood sample syringe, a platelet agonist syringe, an analysis solution syringe, a blood mixing device, and a sample needle cleaner;
    the sampling needle, which is movable, connects with the blood sample syringe, and the sampling needle and the blood sampling syringe are configured to draw a whole blood sample from an associated test tube;
    the sampling needle is movable into the sampling vessel for injecting the whole blood sample into the sampling vessel for storing the whole blood sample in the sampling vessel;
    the blood mixing device which is an air pump is connected with the sampling vessel, the preparation vessel and the analysis vessel for mixing blood samples in the sampling vessel, the preparation vessel and the analysis vessel;
    the platelet agonist syringe is connected with a platelet agonist storage container and the sampling vessel for dispensing so as to dispense platelet agonist into the sampling vessel;
    the analysis solution syringe is connected with an analysis solution storage container, the preparation vessel and the analysis vessel for dispensing so as to dispense analysis solution into the preparation vessel for preparing a first blood sample dilution and for dispensing the analysis solution into the analysis vessel for preparing a second blood sample dilution;
    the sampling needle, the blood sample syringe, the platelet agonist syringe and the analysis solution syringe are driven by motors separately;
    the sampling needle is connected to the blood sample syringe and the analysis solution syringe through pipes and valves respectively;
    as with the blood sample syringe is connected to the sampling needle, blood sample syringe and the sampling needle are configured to transfer
    the blood samples from the associated test tube to the sampling vessel, absorb a partial blood sample from the sampling vessel and transferring transfer the partial blood sample to the preparation vessel; absorb the first diluted blood sample from the preparation vessel and transfer the first diluted blood sample to the analysis vessel; the analysis vessel is connected with the analysis solution container such that
    analysis solution contained in the analysis solution container is deliverable to the analysis
    vessel for preparing a second blood sample dilution, and the analysis vessel includes a quantitative device for platelet number measure; and needle, the sampling needle is movable to the sample needle cleaner for cleaning.

2. The automated platelet function analyzer according to claim 1, wherein the air pump is separately connected to the sampling vessel, the preparation vessel and the analysis vessel through pipes and valves;

the pipe, which is connected to the sampling vessel, has an internal diameter of about 0.2 mm to about 2 mm, and the inlet air flow rate is about 1 to about 20 ml/min.

3. The automated platelet function analyzer according to claim 2, wherein the air pump is a rotary pump or a mixing syringe.

4. The automated platelet function analyzer according to claim 1, further comprising a waste liquid pump connected to the sampling vessel, the preparation vessel, the analysis vessel and the sample needle cleaner.

* * * * *